US009361875B2

(12) United States Patent
Meredith et al.

(10) Patent No.: US 9,361,875 B2
(45) Date of Patent: Jun. 7, 2016

(54) SELECTIVE SUPPRESSION OF AUDIO EMITTED FROM AN AUDIO SOURCE

(71) Applicant: AT&T Mobility II LLC, Atlanta, GA (US)

(72) Inventors: Sheldon Kent Meredith, Marietta, GA (US); Jeremy Fix, Acworth, GA (US); Mario Kosseifi, Roswell, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 230 days.

(21) Appl. No.: 14/087,343

(22) Filed: Nov. 22, 2013

(65) Prior Publication Data

US 2015/0146878 A1 May 28, 2015

(51) Int. Cl.

| | |
|---|---|
| ***A61F 11/06*** | (2006.01) |
| ***G10K 11/16*** | (2006.01) |
| ***H03B 29/00*** | (2006.01) |
| ***G10K 11/178*** | (2006.01) |

(52) U.S. Cl.

CPC ...... *G10K 11/178* (2013.01); *G10K 2210/1081* (2013.01); *G10K 2210/3044* (2013.01)

(58) Field of Classification Search

CPC .................... G10K 2210/1081; G10K 11/178; G10K 2210/108; G10K 2210/3044

USPC ....................................... 381/71.6, 71.1, 71.2

See application file for complete search history.

(56) References Cited

U.S. PATENT DOCUMENTS 5,001,763 A 3/1991 Moseley
5,182,774 A 1/1993 Bourk
5,815,582 A 9/1998 Claybaugh et al.
5,937,070 A 8/1999 Todter et al.
6,118,878 A 9/2000 Jones
6,434,398 B1 8/2002 Inselberg
7,065,219 B1 6/2006 Abe et al.
7,797,005 B2 9/2010 Inselberg
8,111,836 B1 2/2012 Graber (Continued)

FOREIGN PATENT DOCUMENTS

WO 2012/012452 1/2012

OTHER PUBLICATIONS

Sherratt et al., "Cancellation of Siren Noise From Two Way Voice Communications Inside Emergency Vehicles," Acoustics, Speech, and Signal Processing, 1999. Proceedings., 1999 IEEE International Conference on vol. 4. IEEE, 1999 (retreived from http://www.mirlab.org/conference_papers/International_Conference/ICASSP%201999/PDF/AUTHOR/IC991087.PDF).

*Primary Examiner* — Paul S Kim

(74) *Attorney, Agent, or Firm* — Hanley, Flight & Zimmerman, LLC

(57) ABSTRACT

Methods, apparatus, systems and articles of manufacture (e.g., physical storage media, such as storage devices and/or storage disks) to implement selective suppression of audio emitted from an audio source are disclosed. Example methods disclosed herein for audio suppression include obtaining, at a first time, reference audio data corresponding to a first audio signal, the first audio signal to be output by an audio source at a second time later than the first time. Such example methods can also include processing the reference audio data to generate a suppression signal to be output by a speaker associated with a user device to suppress the first audio signal when received at the user device at a third time later than the first time. Such example methods can further include providing the suppression signal to an audio output driver in communication with the speaker.

20 Claims, 7 Drawing Sheets

(56) References Cited

U.S. PATENT DOCUMENTS

| | | | |
|---|---|---|---|
| 8,249,265 B2 | 8/2012 | Shumard | |
| 8,442,428 B2 | 5/2013 | Tan et al. | |
| 8,477,955 B2 * | 7/2013 | Engle ................. | G10K 11/1788 379/430 |
| 2002/0001392 A1 | 1/2002 | Isono et al. | |
| 2004/0109570 A1 | 6/2004 | Bharitkar et al. | |
| 2005/0232435 A1 | 10/2005 | Stothers et al. | |
| 2007/0223714 A1 | 9/2007 | Nishikawa | |
| 2007/0297620 A1 | 12/2007 | Choy | |
| 2010/0235466 A1 | 9/2010 | Jung et al. | |
| 2010/0322433 A1 | 12/2010 | Hsieh | |
| 2010/0329480 A1 | 12/2010 | Boone | |
| 2012/0274775 A1 | 11/2012 | Reiffel | |
| 2013/0129103 A1 | 5/2013 | Donaldson | |
| 2013/0236040 A1 | 9/2013 | Crawford et al. | |

* cited by examiner

SELECTIVE SUPPRESSION OF AUDIO EMITTED FROM AN AUDIO SOURCE

FIELD OF THE DISCLOSURE

This disclosure relates generally to audio processing and, more particularly, to selective suppression of audio emitted from an audio source.

BACKGROUND

Many scenarios exist in which audio is intentionally broadcast via the speakers of an audio source for the benefit of listeners in a geographic area. For example, audio announcements and/or music may be broadcast by a public address system of a venue to provide information and/or entertainment for the benefit of attendees of a sporting event, concert, etc. As another example, loudspeakers may be used by law enforcement and/or military personnel to provide directives, public safety announcements, etc., for purposes of crowd control in a public area. In at least some such scenarios, the audio broadcast by the audio source is emitted by the source's speakers at a volume level intended to make the broadcasted audio audible over other audio in the geographic area.

BRIEF DESCRIPTION OF THE DRAWINGS

Wherever possible, the same reference numbers will be used throughout the drawing(s) and accompanying written description to refer to the same or like parts, elements, etc.

DETAILED DESCRIPTION

Figure 1:
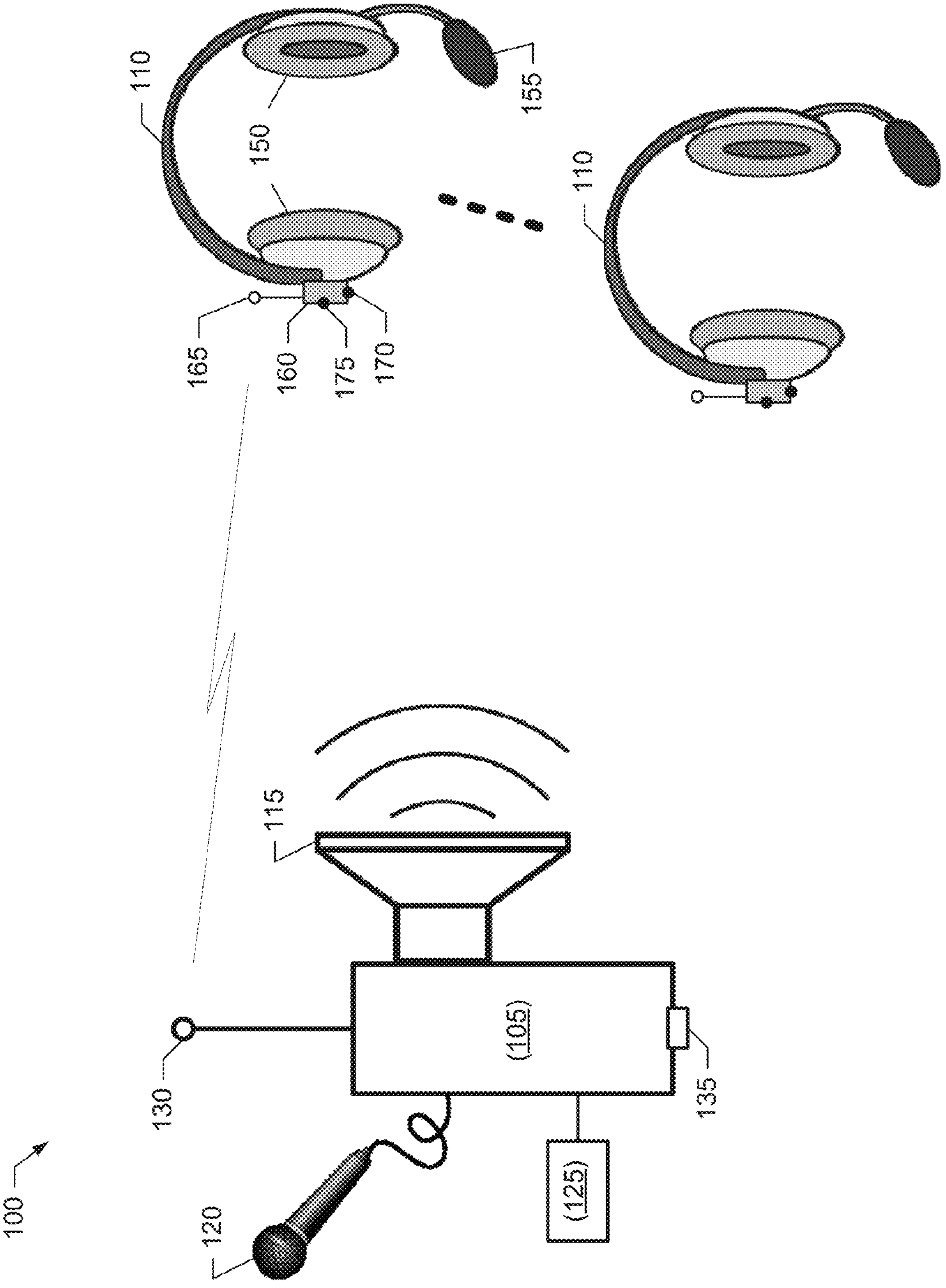
FIG. 1 is a block diagram of an example audio suppression system including an audio source and one or more user devices collectively supporting selective suppression of audio emitted from the audio source, as disclosed herein.

Methods, apparatus, systems and articles of manufacture (e.g., physical storage media, such as storage devices and/or storage disks) to implement selective suppression of audio emitted from an audio source are disclosed herein. As noted above, scenarios exist in which audio broadcast by an audio source is emitted by the source's speakers at a volume level intended to make the broadcasted audio audible over other audio in a geographic area. For example, audio broadcast by a public address system of a venue may emanate from the system's speakers at a high audio volume level to enable the broadcasted audio to be heard by venue attendees over other audio, such as conversations, background music, acoustic noise, etc., in the vicinity of the attendees. Similarly, audio broadcast by government personnel using loudspeakers may emanate from the loudspeakers at a high audio volume level to enable the broadcasted audio to be heard by a crowd over other audio, such as conversations, background music, acoustic noise, etc., in the vicinity of loudspeakers.

However, in at least some scenarios, it may be desirable to be able to selectively suppress the audio emitted from such an audio source for specific personnel in the vicinity of the audio source. For example, at a sporting event, an audio suppression system that could suppress the audio emitted from a public address system for players, coaches and/or referees would enable the players, coaches and/or referees to hear each other on the playing field and reduce the distractions caused by the public address system. As another example, in crowd control scenarios, an audio suppression system that could suppress the audio emitted from the loudspeakers for government personnel (e.g., such as law enforcement and/or military personnel) would permit the government personnel performing crowd control to better communicate with each other.

Selective suppression of audio emitted from an audio source, as disclosed herein, can solve the problem of how to suppress audio emitted from the audio source for selected personnel. As disclosed in further detail below, an example audio suppression system implemented according to examples disclosed herein includes an audio source and one or more user devices, such as headsets, supporting selective audio suppression. At a high-level, in such an example audio suppression system, the audio source informs the user device(s) (e.g., headset(s)) of the audio that will be output by the source prior to this audio being emitted by the source's speakers. The user device(s) (e.g., headset(s)), in turn, use the prior knowledge of the source's output audio to perform selective audio suppression of the audio emanating from the audio source, while permitting the user (e.g., wearer of the headset) to hear other audio in the vicinity of the user.

Example methods for selective audio suppression that can be performed at an example user device (e.g., such as a headset, a media device, a special-purpose audio device, etc.) in an example audio suppression system such as the one mentioned above can include obtaining, at a first time, reference audio data corresponding to a first audio signal, which is to be output by an audio source at a second time later than the first time. Such example methods can also include processing the reference audio data to generate a suppression signal to be output by a speaker associated with the user device to suppress the first audio signal when received at the user device at a third time later than the first time. The third time can be substantially the same as the second time, or the third time can be different from (e.g., later than) the second time (e.g., due to an audio propagation delay between the audio source and the user device). Such example methods can further include providing the suppression signal to an audio output driver in communication with the speaker.

In some such example methods, the obtaining of the reference audio data includes receiving the reference audio data wirelessly from the audio data source. In such example methods, the processing of the reference audio data can include (1) delaying the reference audio data by a first time delay, which is a constant value set to compensate for an expected time interval between the first time and the second time, and (2) inverting the reference audio data. In some such example methods, the processing of the reference audio data can also include (3) estimating a second time delay determined to compensate for an audio propagation delay between the audio source and the user device, the audio propagation delay corresponding to a difference between the second time and the third time, (4) delaying the reference audio data by the first time delay and the second time delay, (5) estimating an audio level of the first audio signal at the user device, and (6) scaling the reference audio data based on the audio level. Some such example methods can further include obtaining sensed audio data from a microphone and/or other audio sensor of the user device. In such example methods, the estimating of the second time delay can include processing the sensed audio data to estimate the audio propagation delay, and the estimating of the audio level includes processing the sensed audio data to estimate the audio level.

Additionally or alternatively, some such example methods further include obtaining configuration data specifying the first time delay, with the configuration data being received wirelessly from the audio source and/or being obtained via a configuration interface of the user device. For example, the configuration data could be received wirelessly with the reference audio data or separately from the reference audio data, or a combination thereof.

Some such example methods further include receiving an activation signal to selectively enable (and disable) the processing of the reference audio data to generate the suppression signal. Additionally or alternatively, some such example methods further include combining the suppression signal with a second audio signal to be output by the speaker. For example, the second audio signal can correspond to media being presented by the user device, an acoustic noise cancellation signal generated by the user device, etc., or any combination thereof.

Example methods for selective audio suppression, which can be performed at an example audio source in an example audio suppression system such as the one mentioned above, can include sending, at a first time, reference audio data in a wireless format to a user device. In such examples, the reference audio data corresponds to a first audio signal that is to be output (e.g., emitted) by the audio source at a second time later than the first time. Such example methods can also include emitting the first audio signal from a speaker associated with the audio source at the second time.

Some such example methods can further include obtaining configuration data specifying a first time delay, which corresponds to a difference between the first time and the second time. Such example methods can also include delaying the first audio signal by the first time delay before emitting the first audio signal from the speaker associated with the audio source.

Additionally or alternatively, some such example methods can further include formatting the reference audio data for wireless transmission to the user device, and sending the reference audio data wirelessly to the user device. Some such example methods can further include sending configuration data wirelessly to the user device, the configuration data specifying a first time delay corresponding to a difference between the first time and the second time. For example, the configuration data can be sent to the user device with the reference audio data. Additionally or alternatively, the configuration data can be sent to the user device separately from the reference audio data.

These and other example methods, apparatus, systems and articles of manufacture (e.g., physical storage media) to implement selective suppression of audio emitted from an audio source are disclosed in greater detail below.

Prior audio cancellation techniques employ headsets that sample an incoming audio signal received by the headset and produce another audio signal 180 degrees out-of-phase with the incoming audio such that the two audio signals partially cancel out in and/or near the wearer's audio canal. For such prior headsets, lower frequencies are easier to cancel simply because the longer wavelength is more forgiving of time delay differences between the audio receivers in the headsets and the position of the audio canal. This is why such prior audio cancellation headsets typically are better at eliminating low frequencies than higher ones. However, prior audio cancellation headsets do not have prior knowledge about the specific incoming audio. Therefore, prior audio cancellation headsets simply measure the audio signal within a particular bandwidth, reproduce the entire signal 180 degrees out of phase, and inject the out-of-phase signal into the audio canal with the goal of cancelling out all sound. In other words, prior audio cancellation headsets cannot support suppressing only a specific audio source but, instead, are limited to suppressing all sound in the vicinity of the wearer without any selectivity.

Unlike such prior audio cancellation headsets, selective audio suppression, as disclosed herein, attempts to selectively suppress specific audio for which prior knowledge exists. Accordingly, selective audio suppression, as disclosed herein, can suppress the audio emanating from a specific audio source, allowing the listener to better focus on other audio sources in the vicinity. Example systems employing selective audio suppression, as disclosed herein, can be useful in many scenarios, such as the example scenarios described above in which audio broadcast by a specific audio source is emitted by the source's speakers at a volume level intended to make the broadcasted audio audible over other audio in the geographic area. For example, government personnel (e.g., such as law enforcement and/or military personnel) can wear headsets implementing selective audio suppression, as disclosed herein, which can provide the benefit of suppressing the loud audio being emitted by a loudspeaker, which is also implementing selective audio suppression as disclosed herein, while still enabling the government personnel to hear voices and/or other sound sources in the vicinity. As another example, referees, coaches and/or players at a sporting event can wear headsets implementing selective audio suppression, as disclosed herein, which can provide the benefit of suppressing the loud audio emanating from a venue's public address system, which is also implementing selective audio suppression as disclosed herein, thereby enabling the referees, coaches and/or players to better hear each other on the playing field.

Turning to the figures, a block diagram of an example audio suppression system 100 implementing selective audio suppression as disclosed herein is illustrated in FIG. 1. The example system 100 of FIG. 1 includes an example audio source 105 and one or more example user devices 110 collectively implementing selective audio suppression as disclosed herein. For example, the audio source 105 and respective ones of the user device(s) 110 can cooperate to achieve suppression of one or more acoustic audio signals (e.g., such as one or more acoustic audio signals output from the audio source 105). The audio source 105 of the illustrated example includes, is coupled to, or is otherwise associated with one or more example speakers 115 configured to emit audio from the audio source 105 that is capable of being heard by one or more listeners in the vicinity of the audio source 105, such as the user(s) of the user device(s) 110. The audio to be emitted by the speaker(s) 115 of the audio source 105 is obtained by one or more example audio input devices included, coupled to, or otherwise associated with the audio source 105. For example, such audio inputs devices may include, but are not limited to, an example microphone 120, an example media source 125, such as a musical keyboard, an musical instrument, a media player, a radio, a television, a computing device, etc., or any combination thereof.

To implement selective audio suppression in accordance with the examples disclosed herein, the example audio source of FIG. 1 also includes, is coupled to, or is otherwise associated with one or more example antenna(s) 130 to permit audio data, which corresponds to the audio to be emitted from the speaker(s) 115 of the audio source 105, to be transmitted wirelessly to the user device(s) 110 prior to the audio actually being emitted from the speaker(s) 115. The audio data transmitted wirelessly via the antenna(s) 130, which is also referred to herein as reference audio data, provides the user device(s) 110 with prior knowledge of the audio signal to be emitted by the audio source 105. As disclosed in further detail below, this prior knowledge can be used by the user device(s) 110 to suppress the audio signal when the audio signal is later emitted by the audio source 105 and received in the vicinity of the user device(s) 110. Although the audio source 105 of the illustrated example is depicted as having the antenna(s) 130, the example audio source 105 can additionally or alternatively have other wireless output devices, such as one or more infrared transmitters, one or more ultrasonic transducers, one or more optical emitters, etc., and/or any combination thereof capable of transmitting the reference audio data wirelessly from the audio source 105 to the user device(s) 110. In some examples, the wireless output device(s) of the audio source 105 are configured or otherwise implemented to transmit the reference audio data wirelessly but non-acoustically such that the reference data is transmitted via any type of wireless signal (e.g., a radio signal, an infrared signal, an optical signal, etc.) other than an acoustic audio signal.

In some examples, the audio source 105 includes one or more example configuration interfaces 135. For example, the configuration interface(s) 135 can include a serial port interface, a universal serial bus (USB) interface, a network interface (e.g., such as an Ethernet interface, a wireless local area network (WLAN) interface, etc.), an optical interface, etc., and/or any combination thereof. In some examples, the configuration interface(s) 135 can include the interface circuit 720 of the example processor platform 700 of FIG. 7, which is described in further detail below. The configuration interface(s) 135 enable any type and/or number(s) of computing devices, such as the example processor platform 700 of FIG. 7, to interface with the audio source 105 to permit configuration of one or more parameters for selective audio suppression. For example, the configuration interface(s) 135 can be used to specify a time delay that is to occur between a first time at which the reference audio data corresponding to an input audio signal (e.g., received from the microphone 120 and/or media source 125) is to be transmitted wirelessly by the audio source 105 (e.g., via the antenna(s) 130) and a second time at which the audio source 105 is to emit the input audio signal from its speaker(s) 115. This time delay is also referred to herein as the audio source time delay. In some examples, the configuration interface(s) 135 can additionally or alternatively be used to specify whether the audio source time delay and/or other configuration information is to be transmitted wirelessly by the audio source 105 (e.g., via the antenna(s) 130) for receipt by the user device(s) 110. For example, the configuration interface(s) 135 can be used to specify whether audio suppression configuration information or a portion thereof, such as the audio source time delay, is be transmitted with the reference audio data transmitted wirelessly by the audio source 105 and/or whether the audio suppression configuration information or a portion thereof, such as the audio source time delay, is be transmitted wirelessly in a signal/message separate from the reference audio data.

The user device(s) 110 in the example audio suppression system 100 of FIG. 1 correspond to example headset(s) 110. An example headset 110 of the illustrated example includes, is coupled to, or is otherwise associated with one or more speaker(s) 150 capable of emitting audio to be heard by a wearer of the headset 110 (or, more generally, to be heard by a user of the user device 110). In some examples, the headset 110 may also include, may be coupled to, or may be otherwise associated with an example microphone 155 to permit a wearer of the headset 110 (or, more generally, a user of the user device 110) to engage in two-way communication.

To implement selective audio suppression as disclosed herein, the example headset 110 also includes an example selective audio suppressor 160. The selective audio suppressor 160 of the illustrated example includes, is coupled to, or is otherwise associated with one or more example antennas 165 to enable the selective audio suppressor 160 to receive the reference audio data transmitted by the audio source 105. As mentioned above and in further detail below, the reference audio data received wirelessly via the antenna(s) 165 at a first time provides the selective audio suppressor 160 with prior knowledge of the audio signal to be emitted by the audio source 105 at a later second time. This prior knowledge is used by the selective audio suppressor 160 to generate a suppression signal to be emitted by the speaker(s) 150 at a later third time to cancel the audio signal emitted by the audio source 105 when it is received in the vicinity of the headset 110. For example, the third time at which the selective audio suppressor 160 causes the suppression signal to be emitted by the speaker(s) 150 may be substantially the same as the second time at which the audio source 105 transmits the audio signal, or later than the second time depending on the audio propagation delay between the audio source 105 and the headset 110. Although the headset 110 of the illustrated example is depicted as having the antenna(s) 165, the example headset 110 can additionally or alternatively have other wireless input devices, such as one or more infrared receivers, one or more ultrasonic transducers, one or more optical detectors, etc., and/or any combination thereof capable of receiving the reference audio data wirelessly from the audio source 105.

In some examples, the selective audio suppressor 160 of the headset 110 includes, is coupled to, or is otherwise associated with an example audio sensor 170 to sense the audio in the vicinity of the headset 110. The audio sensor 170 can be implemented by any type of microphone, acoustic pickup, transducer, etc. In such examples, the selective audio suppressor 160 can use the audio sensed by the audio sensor 170 to further process the reference audio data received via the antenna(s) 165 to generate the suppression signal to be emitted by the speaker(s) 150. For example, the selective audio suppressor 160 may invert the reference audio data received via the antenna(s) 165 and delay the inverted reference audio data by a time delay specified or otherwise determined to correspond to the difference between the first time and the third time described above. Additionally, in examples in which the audio sensor 170 is present, the selective audio suppressor 160 can further adjust the gain and the delay of the inverted reference audio data based on the sensed audio in the vicinity of the headset 110 (which will include the audio emitted from the audio source 105) to improve the audio suppression capability of the suppression signal generated by the selective audio suppressor 160.

In some examples, the selective audio suppressor 160 of the headset 110 additionally or alternatively includes, is coupled to, or is otherwise associated with an example suppression activator 175 to enable a wearer of the headset 110 to selectively enable or disable selective audio suppression in the headset 110. For example, the suppression activator 175 can be implemented by any type of switch, sensor, input device, etc., capable of receiving an input from the wearer of the headset 110 to selectively enable or disable operation of the selective audio suppressor 160 to generate the suppression signal and/or to cause the suppression signal to be emitted by the speaker(s) 150. In some examples, the suppression activator 175 additionally or alternatively permits selection of one or more of a group of audio sources 105 for which selective audio suppression is to be performed. For example, the audio source 105 may include source identification information, such as a name, address, etc., and/or any other type or combination of identifiers of the audio source 105, with the reference audio data transmitted by the audio source 105. In such examples, if multiple audio sources 105 are included in the example audio suppression system 100, the respective source identification information included with the reference audio data transmitted by the respective audio sources 105 can be used to select the reference audio data and, thus, the audio source 105 to be processed by the selective audio suppressor 160 to generate the suppression signal. In such examples, the suppression activator 175 can be used to select among (e.g., cycle through) the available reference audio data (e.g., by using the identification information included with the reference audio data) to selectively suppress the audio emitted from particular one(s) of the audio sources 105.

In an example operation of the audio suppression system 100, the audio to be amplified and output by the audio source 105 is electronically sampled in the audio source 105 to generate reference audio data. The reference audio data is sent via the source's antenna(s) 130 to the headset 110 prior to the audio being output from the speaker(s) 115 of the audio source 105. The headset 110 receives the wireless signal containing the source's reference audio data and then reconstructs the audio waveform prior to the audio signal being output by the speaker(s) 115 of the audio source 105. After a finite delay (e.g., tens of milliseconds, or any other amount of time), the speaker(s) 115 of the audio source 105 output the acoustic audio waveform corresponding to the reference audio data previously sent to the headset 110. The audio sensor 170 of the headset 110 receives the incoming acoustic audio waveform. The headset 110, having prior knowledge of the reference audio data, is able to time synchronize the reference audio data previously provided by the audio source 105 with the incoming acoustic audio waveform in real time. This compensates for the propagation delay between the audio source 105 and the headset 110. In some examples, the headset also employs equalization techniques to discern multiple copies of the acoustic audio signal emitted from the audio source 105, such as may occur due to the acoustic audio signal emitted from the audio source 105 experiencing multiple bounces from objects, in addition to the line of sight propagation path. Because the headset 110 is informed of the source's audio signal before it arrives, the headset 110 can produce an acoustic suppression signal, which is transmitted by the headset's speaker(s) 150 into the audio canal of the wearer. This can cause selective audio suppression of only the audio signal emitted from the speaker(s) 115 of the selected audio source 105, with little to no effect on the other sources of audio in the vicinity of the wearer. In some examples, the comparison between the incoming acoustic audio and the waveform reconstructed from the received reference audio data can adapt dynamically to compensate for the absolute acoustic power level in real time. For example, if the wearer rotates her head such that the incoming acoustic audio level changes, the headset 110 may also change the power level of the audio suppression signal to maintain optimal audio signal suppression.

The example audio suppression system 100 of FIG. 1 is illustrated as including one audio source 105 and two user devices 110, which are implemented as example headsets 110. However, the audio suppression system 100 is not limited thereto. For example, the example audio suppression system 100 can support selective audio suppression for any number and/or type(s) of audio source(s) 105 and/or user device(s) 110. Also, although the example user device(s) 110 of FIG. 1 are depicted as being headset(s) 110, the user device(s) 110 can alternatively be implemented by any other type(s) and/or number of user device(s). For example, a user device 110 in the example system 100 of FIG. 1 can be implemented by a media device, such as a computing device (e.g., personal computer, a tablet computer, a smartphone, etc.), a media player (e.g., such as a digital versatile disk (DVD) player, an MP3 player, etc.) and/or any other device (e.g., such as the example processor platform 700 of FIG. 7) having the capability to output audio via speaker(s) (e.g., the speaker(s) 150) and adapted to include or otherwise implement the example selective audio suppressor 160. Furthermore, in some examples, a user device 110 can be implemented by a special-purpose audio device constructed to include the selective audio suppressor 160 and associated functionality disclosed herein.

Figure 2:
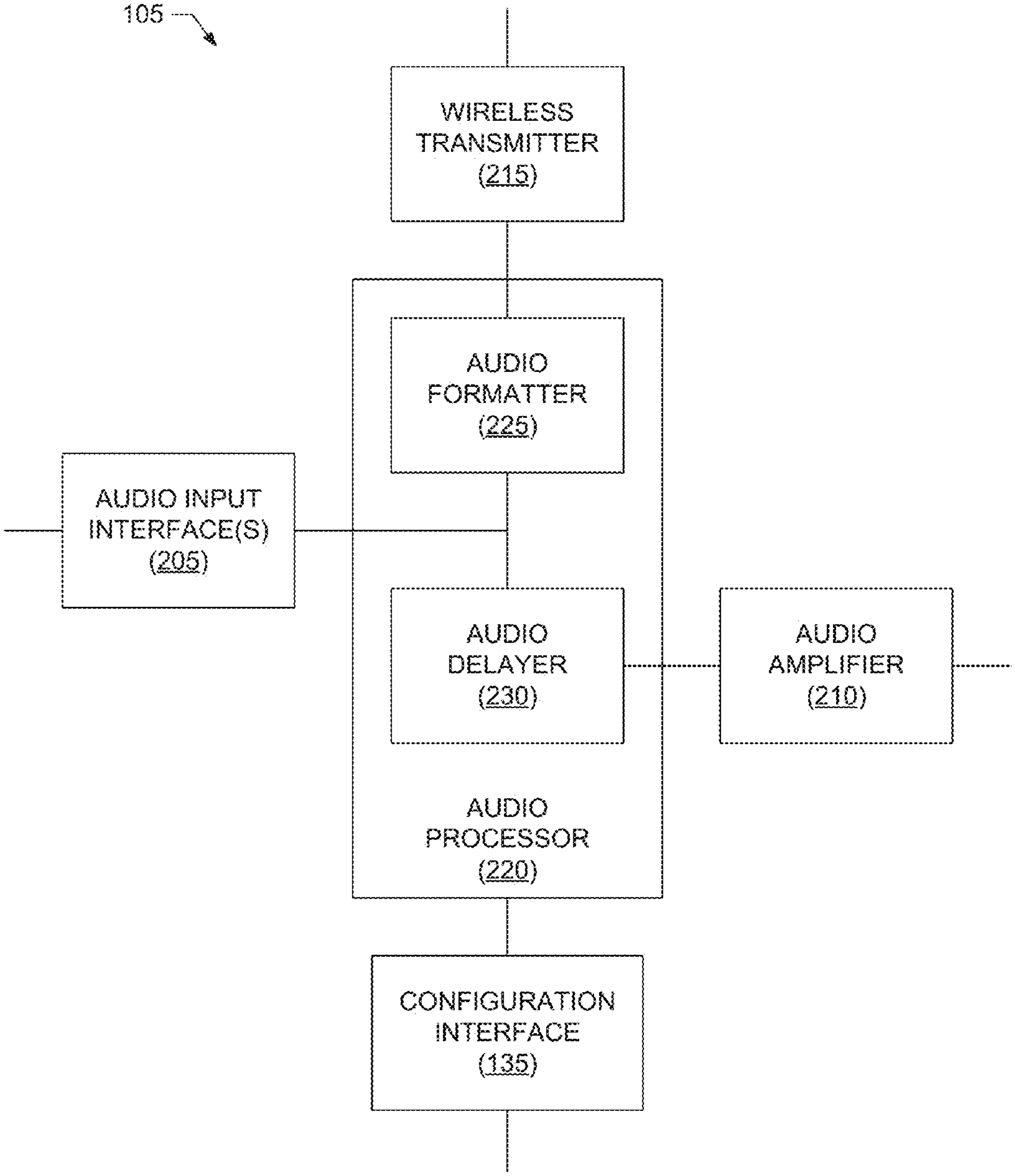
FIG. 2 is a block diagram of an example audio source that can be used to implement the example system of FIG. 1.

A block diagram of an example implementation of the audio source 105 of FIG. 1 is illustrated in FIG. 2. The example audio source 105 of FIG. 2 includes one or more example audio input interfaces 205 to interface with one or more audio input devices providing audio to be output by the audio source 105. For example, the audio input interface(s) 205 can be implemented by any number and/or type(s) of interfaces capable of obtaining input audio from the example microphone 120, the example media source 125, such as a musical keyboard, an musical instrument, a media player, a radio, a television, a computing device, etc., or any combination thereof.

The example audio source 105 of FIG. 2 also includes an example audio amplifier 210 to drive the speaker(s) 115 of the audio source 105, and an example wireless transmitter 215 to enable data to be transmitted wirelessly using the antenna(s) 130 of the audio source 105. For example, the audio amplifier 210 can be implemented by any type of audio amplification circuitry capable of driving the speaker(s) 115 at a power level sufficient to achieve a desired acoustic volume level for the audio emitted from the audio source 105. The wireless transmitter 215 can be implemented to be compliant with any type(s) and/or number of communication protocols capable of transmitting data wirelessly to a remote receiver, such as the example user device 110.

The example audio source 105 of FIG. 2 further includes an example audio processor 220 to process the input audio obtained by the audio input interface(s) 205 to implement selective audio suppression as disclosed herein. In the illustrated example of FIG. 2, the audio processor 220 includes an example audio formatter 225 to format the input audio for wireless transmission via the wireless transmitter 215. For example, the audio formatter 225 may sample and digitize the input audio to form reference audio data (e.g., such as pulse code modulation (PCM) data samples or audio data represented in any other appropriate format). The audio formatter 225 may also group the reference audio data into packets and encode the packet for transmission according to any type of wireless communication protocol. In some examples, the audio formatter 225 may add source identification information to the formatted reference audio data to enable the reference audio data to be uniquely associated with the audio source 105 (e.g., to permit selection of the reference audio data associated with the audio source 105 from among a group of reference audio data broadcast wirelessly from a group of audio sources 105.) In the illustrated example, the reference audio data formatted by the audio formatter 225 is transmitted wirelessly by the wireless transmitter 215 for receipt by any user device(s) within range of the audio source 105.

The example audio processor 220 of FIG. 2 also includes an example audio delayer 230 to delay the input audio obtained via the audio interface(s) prior to providing the audio to the audio amplifier 210 driving the speaker(s) (e.g., the speaker(s) 115) of the audio source 105. In the illustrated example, the audio delayer 230 is configured to apply a time delay to the input audio, which may be a fixed time delay, a selectable time delay, a programmable time delay, etc. The audio delayer 230 applies the time delay to the input audio to provide time for user device(s), such as the user device(s) 110, to receive and process the reference audio data transmitted wirelessly by the wireless transmitter 215 before the delayed audio signal is provided to the audio amplifier 210 for output by the speaker(s) of the audio source 105.

The example audio source 105 of FIG. 2 also includes the example configuration interface(s) 135 described above in connection with FIG. 1 to permit configuration of one or more parameters for selective audio suppression processing in the audio source 105. For example, the configuration interface(s) 135 can be used to specify the time delay to be applied by the audio delayer 230. As described above, the time delay applied by the audio delayer 230 corresponds to the time between a first time at which the reference audio data corresponding to an input audio signal (e.g., obtained via the audio input interface(s) 205) is to be transmitted wirelessly by the wireless transmitter 215 and a second time at which the input audio signal is to be applied to the audio amplifier 210 and output by the speaker(s) 115 of the audio source 105. In some examples, the configuration interface(s) 135 can additionally or alternatively be used to specify whether a value of the time delay applied by the audio delayer 230 is to be transmitted wirelessly by the wireless transmitter 215 to enable the value of this audio delay to be conveyed to the user device(s) 110 in range of the audio source 105. In such examples, the configuration interface(s) 135 can further be used to specify whether the value of the time delay is to be transmitted with the reference audio data or separately from the audio data. Additionally or alternatively, in some examples, the configuration interface(s) 135 can be used to specify the identification information to be included by the audio formatter 225 in the reference audio data to be transmitted wirelessly via the wireless transmitter 215.

Figure 3:
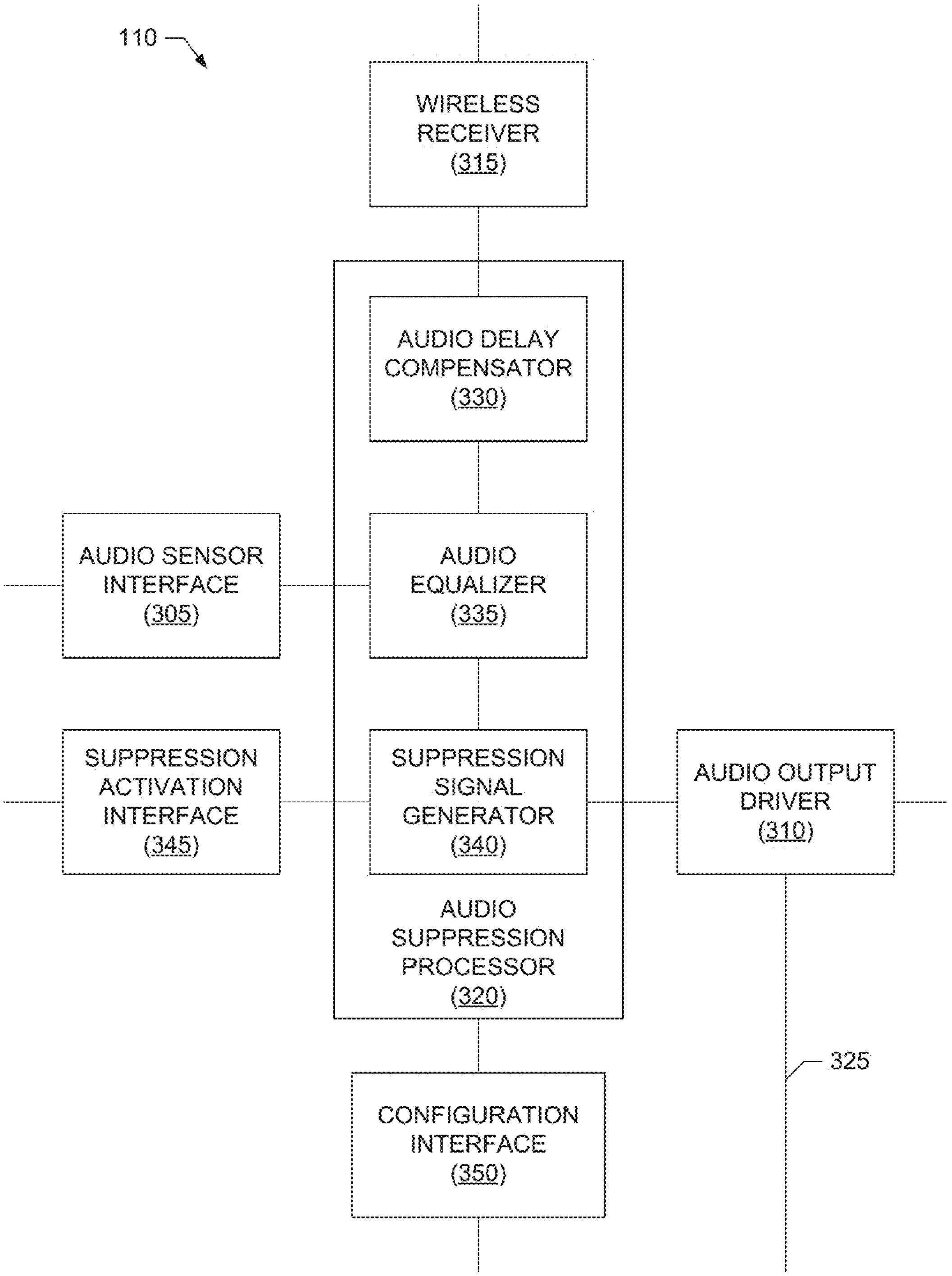
FIG. 3 is a block diagram of an example user device that can be used to implement the example system of FIG. 1.

A block diagram of an example implementation of the user device 110 of FIG. 1 is illustrated in FIG. 3. The example user device 110 of FIG. 3 includes an example audio sensor interface 305 to interface with one or more audio sensors, such as the audio sensor 170, of the user device 110. For example, the audio input interface(s) 205 can be implemented by any number and/or type(s) of interfaces capable of obtaining input audio from microphone(s), acoustic pickup(s), transducer(s), etc., or combination thereof. In the illustrated example, the audio sensor interface 305 obtains, from the audio sensor(s) 170, audio data representative of the sensed audio in the vicinity of the user device 110. For example, the sensed audio data obtained from the audio sensor interface 305 can include audio signal(s) being emitted by one or more audio source(s), such as the audio source 105.

The example user device 110 of FIG. 3 also includes an example audio output driver 310 to drive the speaker(s) 150 of the user device 110, and an example wireless receiver 315 to enable data to be received wirelessly using the antenna(s) 165 of the user device 110. For example, the audio output driver 310 can be implemented by any type of audio amplification circuitry capable of driving the speaker(s) 150 at a power level sufficient to achieve a desired acoustic volume level for the audio emitted from the user device 110. The wireless receiver 315 can be implemented to be compliant with any type(s) and/or number of communication protocols capable of receiving data wirelessly from a remote transmitter, such as the example audio source 105.

The example user device 110 of FIG. 3 further includes an example audio suppression processor 320 to process reference audio data obtained via the wireless receiver 315 and sensed audio data obtained via the audio sensor interface 305 to generate a suppression signal to be provided to the audio output driver 310. This suppression signal is then emitted by the speaker(s) 150 being driven by the audio output driver 310 to suppress the audio signal being emitted by the audio source, such as the audio source 105, that provided the reference audio data received via the wireless receiver 315. In some examples, the audio output driver 310 (and/or the audio suppression processor 320) combines the generated suppression signal with a local audio signal 325, which may correspond to media being presented by the user device 110, an acoustic noise cancellation signal generated by the user device 110 using any type of acoustic noise cancellation technology, etc., or any combination thereof. For example, the audio signal 325 can correspond to an audio portion of video or music being played by the user device 110, an audio portion of a phone conversation, chat conversation, etc., being provided by the user device 110, etc.

In the illustrated example of FIG. 3, the audio suppression processor 320 includes an example audio delay compensator 330 to compensate for the delay between a first time at which the reference audio data is received via the wireless receiver 315 and a second time at which the audio source (e.g., the audio source 105) providing the reference audio data is to emit the audio signal corresponding to the reference audio data. Accordingly, the audio delay compensator 330 delays the reference audio data by a first time delay that is representative of the difference between the first time at which the reference audio data is received via the wireless receiver 315 and the second time at which the audio source is to emit the audio signal corresponding to the reference audio data. In some examples, a value of this first time delay is obtained from data received from the audio source via the wireless receiver 315. For example, the first time delay can be specified by the audio source and (1) included with the wireless transmission containing the reference audio data and/or (2) transmitted wirelessly in a separate configuration message. In some examples, the value of this first time delay is specified as configuration data provided to or programmed into the user device 110.

The example audio suppression processor 320 of FIG. 3 also includes an example audio equalizer 335 to estimate a gain to be applied to the reference audio data when generating the suppression signal. In the illustrated example, the audio equalizer 335 obtains the sensed audio data from the audio sensor interface 305 and the reference audio data from the wireless receiver 315 (possibly after processing by the audio compensator 330) and compares the sensed audio data with the reference audio data to estimate an audio level of the audio signal being received from the corresponding audio source (e.g., the audio source 105) in the vicinity of the user device 110. For example, the audio equalizer 335 can use any type(s) and/or number of correlation techniques, comparison techniques, equalization techniques, etc., to compare the sensed audio data with past and/or present reference audio data to estimate the audio level as a gain factor that can be applied to the reference audio data to cause the reference audio data to have an audio level similar to the sensed audio data.

In some examples, the audio equalizer 335 further estimates a second time delay corresponding to the audio propagation delay between the audio source (e.g., the audio source 105) providing the reference audio data and the user device 110. For example, the audio equalizer 335 can use any type(s) and/or number of correlation techniques, comparison techniques, equalization techniques, etc., to compare the sensed audio data with past and/or present reference audio data (e.g., after having been subjected to the first delay by the audio delay compensator 330) to estimate the second time delay as a further delay that would cause the reference audio data to align with (e.g., match) the sensed audio data. In some examples, the audio equalizer 335 implements equalization techniques capable of determining multiple gain factors and propagation delays capable of accounting for multiple audio propagation paths resulting from the audio signal emitted by an audio source (e.g., the audio source 105) experiencing multiple bounces from objects in addition to, or as an alternative to, propagation along a line of sight propagation path to the user device 110.

The example audio suppression processor 320 of FIG. 3 further includes an example suppression signal generator 340 to generate the suppression signal to be applied to the audio output driver 310 that is driving the speaker(s) 150 of the user device. In the illustrated example of FIG. 3, the suppression signal generator 340 generates the suppression signal by inverting the reference audio data received via the wireless receiver 315. In some examples, the suppression signal generator 340 inverts the reference audio data before or after the reference audio data has been subjected to the first time delay by the audio compensator 330. Also, in some examples, the suppression signal generator 340, before or after inverting the reference audio data, further delays (e.g., in addition to the first time delay) the reference audio data by the second time delay determined by the audio equalizer 335 to be representative of the propagation delay between the audio source and the user device 110, and scales the reference audio data by a gain factor determined by the audio equalizer 335 to be representative of the audio level of the audio signal of the audio source as received in the vicinity of the user device 110. In some examples, the suppression signal generator 340 applies a combination (e.g., superposition) of multiple gain factors and/or propagation delays, as determined by the audio equalizer 335, to even further align the reference audio data with the corresponding audio signal to be received from the audio source 105 prior to generating the suppression signal.

The example user device 110 of FIG. 3 also includes an example suppression activation interface 345 to interface with the example suppression activator 175 of the user device 110 to enable a user to selectively enable or disable operation of the audio suppression processor 320. For example, upon receiving an enable signal from the suppression activator 175, the suppression activation interface 345 can activate the audio suppression processor 320 and the elements included in the audio suppression processor 320 (e.g., such as the audio delay compensator 330, the audio equalizer 335 and the suppression signal generator 340). In some examples, upon receiving a disable signal from the suppression activator 175, the suppression activation interface 345 can deactivate the audio suppression processor 320 and all of its elements in their entirety, or one or more of the elements in the audio suppression processor 320. For example, upon receiving a disable signal, the suppression activation interface 345 could deactivate just the suppression signal generator 340 but keep the audio delay compensator 330 and the audio equalizer 335 active to permit the audio equalization procedure to keep executing and, thereby, maintain an accurate estimate of the acoustic surroundings of the user device 110.

In some examples, the suppression activation interface 345 also supports selection from among multiple audio sources that is/are to have their respective audio signals suppressed at the user device 110. For example, the suppression activation interface 345 can receive data from the suppression activator 175 specifying an identifier for a particular audio source whose audio signal is to be suppressed, or indicating that the suppression activation interface 345 should select the next available audio source from among a set of audio sources for which reference audio data and source identification has been received via the wireless receiver 315. The latter selection technique permits a user to cause the user device 110 to cycle through suppressing different available audio sources until a desired source is reached, without requiring prior knowledge of the identification information for the different audio sources. As described above, the reference audio data obtained via the wireless receiver 315 can include source identification information to permit the received reference audio data to be associated with a respective audio source (e.g., such as the audio source 105).

The example user device 110 of FIG. 3 may also include an example configuration interface 350 to enable the configuration of one or more parameters for selective audio suppression, such as the first time delay described above, which is representative of the difference between the first time at which the reference audio data is received via the wireless receiver 315 and the second time at which the audio source providing the reference audio data is to emit an audio signal corresponding to the reference audio data. For example, the configuration interface 350 can include a serial port interface, a universal serial bus (USB) interface, a network interface (e.g., such as an Ethernet interface, a wireless local area network (WLAN) interface, etc.), an optical interface, etc., and/or any combination thereof. In some examples, the configuration interface 350 can include the interface circuit 720 of the example processor platform 700 of FIG. 7, which is described in further detail below.

While example manners of implementing the audio suppression system 100 are illustrated in FIGS. 1-3, one or more of the elements, processes and/or devices illustrated in FIGS. 1-3 may be combined, divided, re-arranged, omitted, eliminated and/or implemented in any other way. Further, the example audio source 105, the example user device(s) 110, the example configuration interface 135, the example audio input interfaces 205, the example audio amplifier 210, the example wireless transmitter 215, the example audio processor 220, the example audio formatter 225, the example audio delayer 230, the example audio sensor interface 305, the example audio output driver 310, the example wireless receiver 315, the example audio suppression processor 320, the example audio delay compensator 330, the example audio equalizer 335, the suppression signal generator 340, the example suppression activation interface 345, the example configuration interface 350 and/or, more generally, the example audio suppression system 100 may be implemented by hardware, software, firmware and/or any combination of hardware, software and/or firmware. Thus, for example, any of the example audio source 105, the example user device(s) 110, the example configuration interface 135, the example audio input interfaces 205, the example audio amplifier 210, the example wireless transmitter 215, the example audio processor 220, the example audio formatter 225, the example audio delayer 230, the example audio sensor interface 305, the example audio output driver 310, the example wireless receiver 315, the example audio suppression processor 320, the example audio delay compensator 330, the example audio equalizer 335, the suppression signal generator 340, the example suppression activation interface 345, the example configuration interface 350 and/or, more generally, the example audio suppression system 100 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example audio suppression system 100, the example audio source 105, the example user device(s) 110, the example configuration interface 135, the example audio input interfaces 205, the example audio amplifier 210, the example wireless transmitter 215, the example audio processor 220, the example audio formatter 225, the example audio delayer 230, the example audio sensor interface 305, the example audio output driver 310, the example wireless receiver 315, the example audio suppression processor 320, the example audio delay compensator 330, the example audio equalizer 335, the suppression signal generator 340, the example suppression activation interface 345 and/or the example configuration interface 350 is/are hereby expressly defined to include a tangible computer readable storage device or storage disk such as a memory, a digital versatile disk (DVD), a compact disk (CD), a Blu-ray disk, etc. storing the software and/or firmware. Further still, the example audio suppression system 100 of FIGS. 1-3 may include one or more elements, processes and/or devices in addition to, or instead of, those illustrated in FIGS. 1-3, and/or may include more than one of any or all of the illustrated elements, processes and devices.

Figure 4:
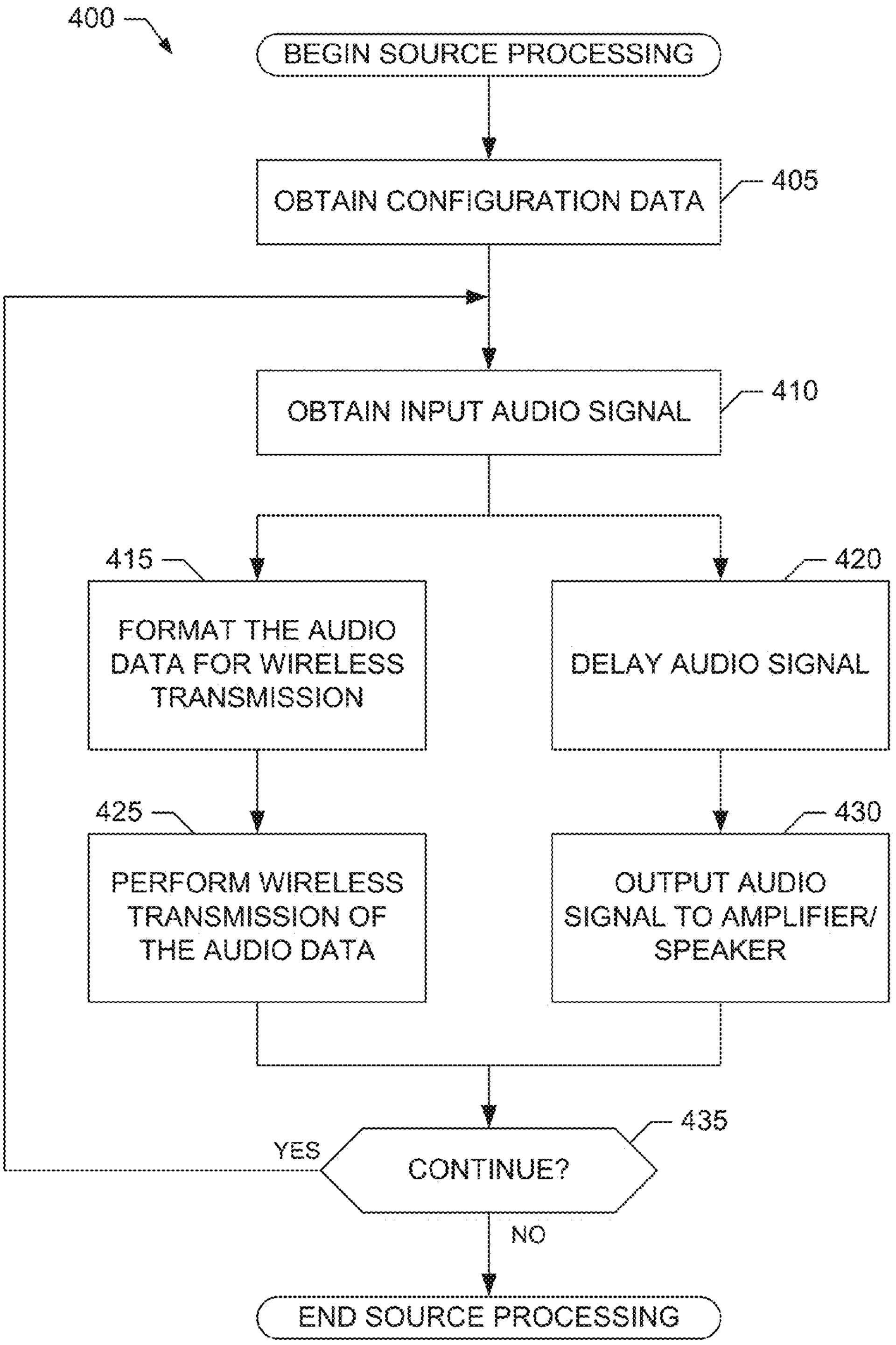
FIG. 4 is a flowchart representative of example machine readable instructions that may be executed to implement the example audio source of FIGS. 1 and/or 2.
Figure 5:
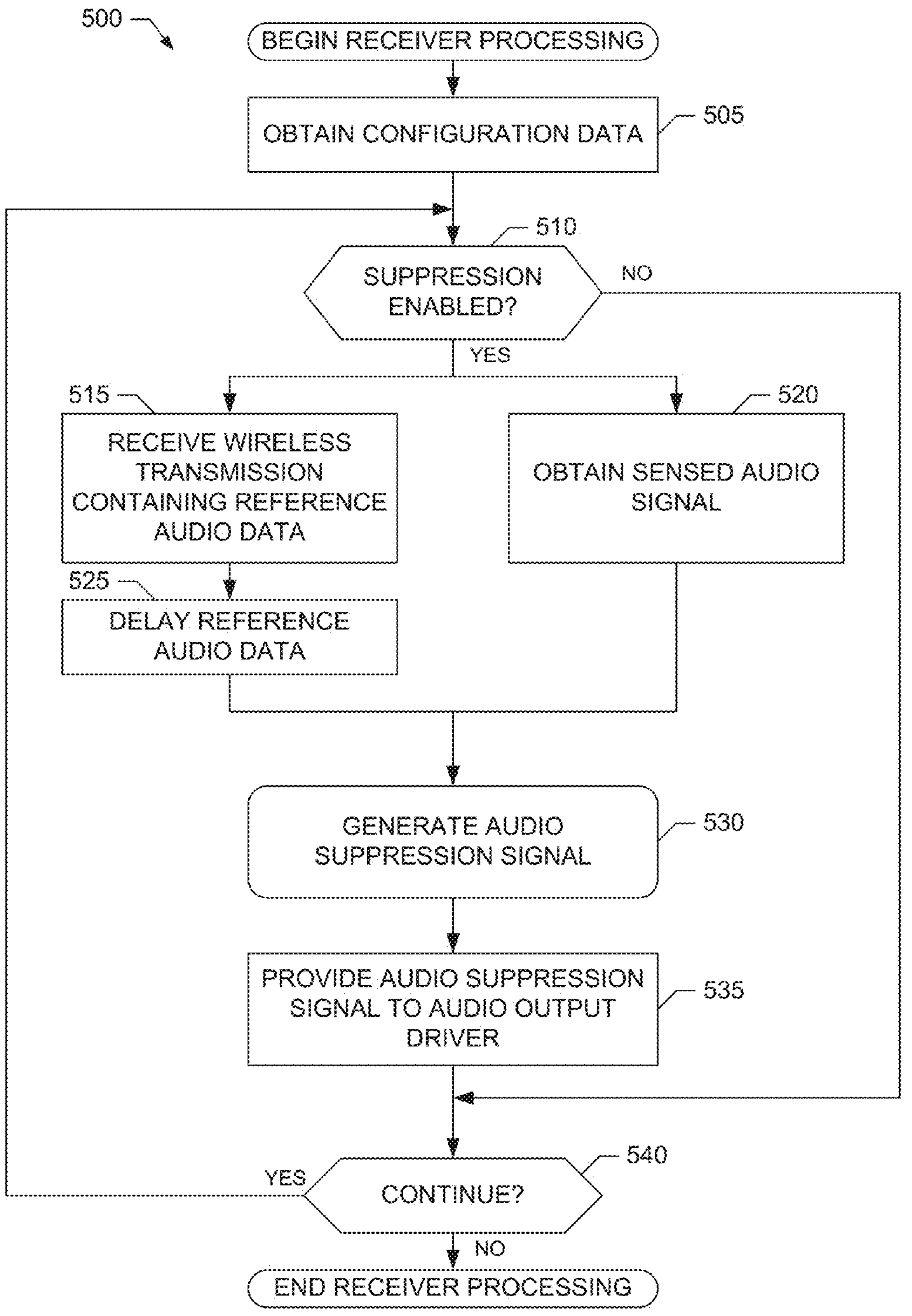
FIG. 5 is a flowchart representative of example machine readable instructions that may be executed to implement the example user device of FIGS. 1 and/or 3.
Figure 6:
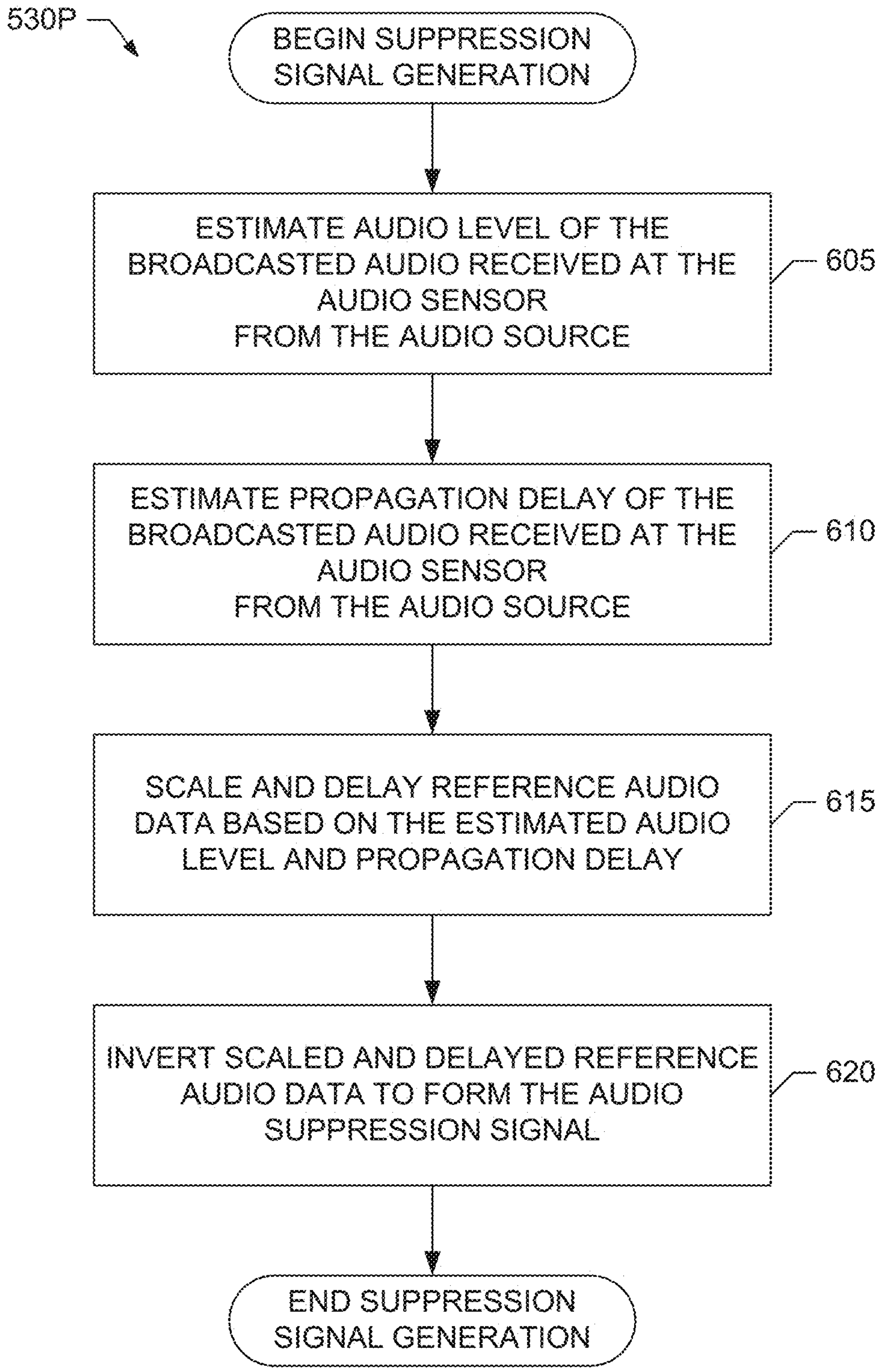
FIG. 6 is a flowchart representative of example machine readable instructions that may be used to implement at least a portion of the example machine readable instructions of FIG. 5, and/or that may be executed to implement an example suppression signal generation procedure at the example user device of FIGS. 1 and/or 3.

Flowcharts representative of example machine readable instructions for implementing the example audio suppression system 100, the example audio source 105, the example user device(s) 110, the example configuration interface 135, the example audio input interfaces 205, the example audio amplifier 210, the example wireless transmitter 215, the example audio processor 220, the example audio formatter 225, the example audio delayer 230, the example audio sensor interface 305, the example audio output driver 310, the example wireless receiver 315, the example audio suppression processor 320, the example audio delay compensator 330, the example audio equalizer 335, the suppression signal generator 340, the example suppression activation interface 345 and/or the example configuration interface 350 are shown in FIGS. 4-6. In these examples, the machine readable instructions comprise one or more programs for execution by a processor, such as the processor 712 shown in the example processor platform 700 discussed below in connection with FIG. 7. The one or more programs, or portion(s) thereof, may be embodied in software stored on a tangible computer readable storage medium such as a CD-ROM, a floppy disk, a hard drive, a digital versatile disk (DVD), a Blu-Ray Disk™, or a memory associated with the processor 712, but the entire program or programs and/or portions thereof could alternatively be executed by a device other than the processor 712 and/or embodied in firmware or dedicated hardware (e.g., implemented by an ASIC, a PLD, an FPLD, discrete logic, etc.). Also, one or more of the machine readable instructions represented by the flowcharts of FIGS. 4-6 may be implemented manually. Further, although the example program(s) is(are) described with reference to the flowcharts illustrated in FIGS. 4-6, many other methods of implementing the example audio suppression system 100, the example audio source 105, the example user device(s) 110, the example configuration interface 135, the example audio input interfaces 205, the example audio amplifier 210, the example wireless transmitter 215, the example audio processor 220, the example audio formatter 225, the example audio delayer 230, the example audio sensor interface 305, the example audio output driver 310, the example wireless receiver 315, the example audio suppression processor 320, the example audio delay compensator 330, the example audio equalizer 335, the suppression signal generator 340, the example suppression activation interface 345 and/or the example configuration interface 350 may alternatively be used. For example, with reference to the flowcharts illustrated in FIGS. 4-6, the order of execution of the blocks may be changed, and/or some of the blocks described may be changed, eliminated, combined and/or subdivided into multiple blocks.

As mentioned above, the example processes of FIGS. 4-6 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 4-6 may be implemented using coded instructions (e.g., computer and/or machine readable instructions) stored on a non-transitory computer and/or machine readable medium such as a hard disk drive, a flash memory, a ROM, a CD, a DVD, a cache, a RAM and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. Also, as used herein, the terms "computer readable" and "machine readable" are considered equivalent unless indicated otherwise.

An example program 400 that may be executed to implement the example audio source 105 of FIGS. 1 and/or 2 is represented by the flowchart shown in FIG. 4. For convenience, and without loss of generality, operation of the example program 400 is described from the perspective of the example audio source 105 of FIG. 2 operating in the example audio suppression system 100 of FIG. 1. With reference to the preceding figures and associated written descriptions, the example program 400 of FIG. 4 begins execution at block 405 at which the configuration interface 135 of the audio source 105 obtains configuration data specifying, for example, one or more parameters for selective audio suppression, as described above. At block 410, the audio input interface(s) 205 of the audio source 105 obtain, from one or more audio input devices, such as the microphone 120, the media source 125, etc., the audio signal that is to be emitted by the audio source 105, as described above. In the illustrated example of FIG. 4, processing then proceeds to blocks 415 and 420 in parallel. However, in other examples, the processing at block 415 and 420 can be invoked serially.

At block 415, the audio formatter 225 of the audio source 105 (or, more generally, the audio processor 220 of the audio source 105) formats the audio signal obtained at block 410 as reference audio data for wireless transmission by the audio source 105, as described above. At block 425, the wireless transmitter 215 of the audio source 105 transmits, as described above, the resulting reference audio data for receipt by any user device(s) in range of the audio source 105, such as one or more of the user devices 110 of FIGS. 1 and/or 3. In parallel, at block 420, the audio delayer 230 of the audio source 105 (or, more generally, the audio processor 220 of the audio source 105) delays the input audio obtained at block 410 by a first time delay, as described above. At block 430, the resulting delayed audio signal, which corresponds to the reference audio data previously transmitted at block 425, is provided to the audio amplifier 210 of the audio source 105 for output by the speaker(s) 115 of the audio source 105.

At block 435, the audio processor 220 of the audio source 105 determines whether processing is to continue. If processing is to continue (block 435), processing returns to block 410 and blocks subsequent thereto. Otherwise, execution of the example program 400 ends.

An example program 500 that may be executed to implement one or more of the example user devices 110 of FIGS. 1 and/or 3 is represented by the flowchart shown in FIG. 5. For convenience, and without loss of generality, operation of the example program 500 is described from the perspective of the example user device 110 of FIG. 3 operating in the example audio suppression system 100 of FIG. 1. With reference to the preceding figures and associated written descriptions, the example program 500 of FIG. 5 begins execution at block 505 at which the configuration interface 350 of the user device 110 obtains configuration data specifying, for example, one or more parameters for selective audio suppression, as described above. At block 510, the suppression activation interface 345 of the user device 110 determines whether selective audio suppression has been enabled. If selective audio suppression has been enabled (block 510), processing then proceeds to blocks 515 and 520 in parallel. However, in other examples, the processing at block 515 and 520 can be invoked serially.

At block 515, the wireless receiver 315 of the user device 110 receives reference audio data from the audio source 105, which corresponds to an audio signal to be emitted by the audio source 105 at a later time, as described above. At block 525, the audio delay compensator 330 of the user device 110 (or, more generally, the audio suppression processor 320 of the user device 110) delays the reference audio data by a first time delay that is representative of the difference between a first time at which the reference audio data is received via the wireless receiver 315 and a second time at which the audio source 105 is to emit the audio signal corresponding to the reference audio data. In parallel, at block 520 the audio sensor interface 305 of the user device 110 obtains, from the audio sensor 170, sensed audio that is representative of the audio in the vicinity of the user device 110.

At block 530, the audio suppression processor 320 of the user device 110 uses the delayed reference audio data obtained at block 525 and the sensed audio data obtained at block 520 to generate, as described above, an audio suppression signal to suppress the audio signal emitted by the audio source 105 and corresponding to the received reference audio data. An example program 530P that may be used to implement the processing at block 530 is illustrated in FIG. 6, which is described in further detail below. At block 535, the audio suppression processor 320 provides the generated audio suppression signal to the audio output driver 310 of the user device 110, which causes the audio suppression signal to be emitted by the speaker(s) 150 of the user device 110.

At block 540, the audio suppression processor 320 of the user device 110 determines whether processing is to continue. If processing is to continue (block 540), processing returns to block 510 and blocks subsequent thereto. Otherwise, execution of the example program 500 ends.

An example program 530P that may be used to implement the processing at block 530 of FIG. 5 and/or that may be executed to implement audio suppression signal generation in the example user devices 110 of FIGS. 1 and/or 3 is represented by the flowchart shown in FIG. 6. For convenience, and without loss of generality, operation of the example program 530P is described from the perspective of the example user device 110 of FIG. 3 operating in the example audio suppression system 100 of FIG. 1. With reference to the preceding figures and associated written descriptions, the example program 530P of FIG. 6 begins execution at block 605 at which the audio equalizer 335 of the user device 110 (or, more generally, the audio suppression processor 320 of the user device 110) uses the reference audio data received via the wireless receiver 315 and the sensed audio obtained via the audio sensor interface 305 to estimate the audio level of the audio emitted from the audio source 105 and received at the audio sensor 170 of the user device 110, as described above. At block 610, the audio equalizer 335 of the user device 110 (or, more generally, the audio suppression processor 320) uses the reference audio data received via the wireless receiver 315 and the sensed audio obtained via the audio sensor interface 305 to estimate the audio propagation delay of the audio source 105 and the user device 110, as described above. At block 615, the suppression signal generator 340 of the user device 110 (or, more generally, the audio suppression processor 320) scales the reference audio data by a gain factor based on the audio level estimated at block 605, and applies a second time delay (e.g., in addition to the first time delay described above) to the reference audio data, which corresponds to the propagation delay estimate at block 610, as described above. At block 620, the suppression signal generator 340 (or, more generally, the audio suppression processor 320) inverts the scaled and delayed reference audio data obtained at block 615 (e.g., if the reference audio data was not already inverted during prior processing) to generate the audio suppression signal to be provided to the audio output driver 310 of the user device 110.

As noted above, in some examples, the audio suppression processor 320 can implement more sophisticated audio equalization procedures to alter the reference audio data to match or closely align with the corresponding audio signal to be emitted by the audio source 105. The resulting equalized reference audio data can then be inverted by the audio suppression processor 320 to generate the audio suppression signal.

Figure 7:
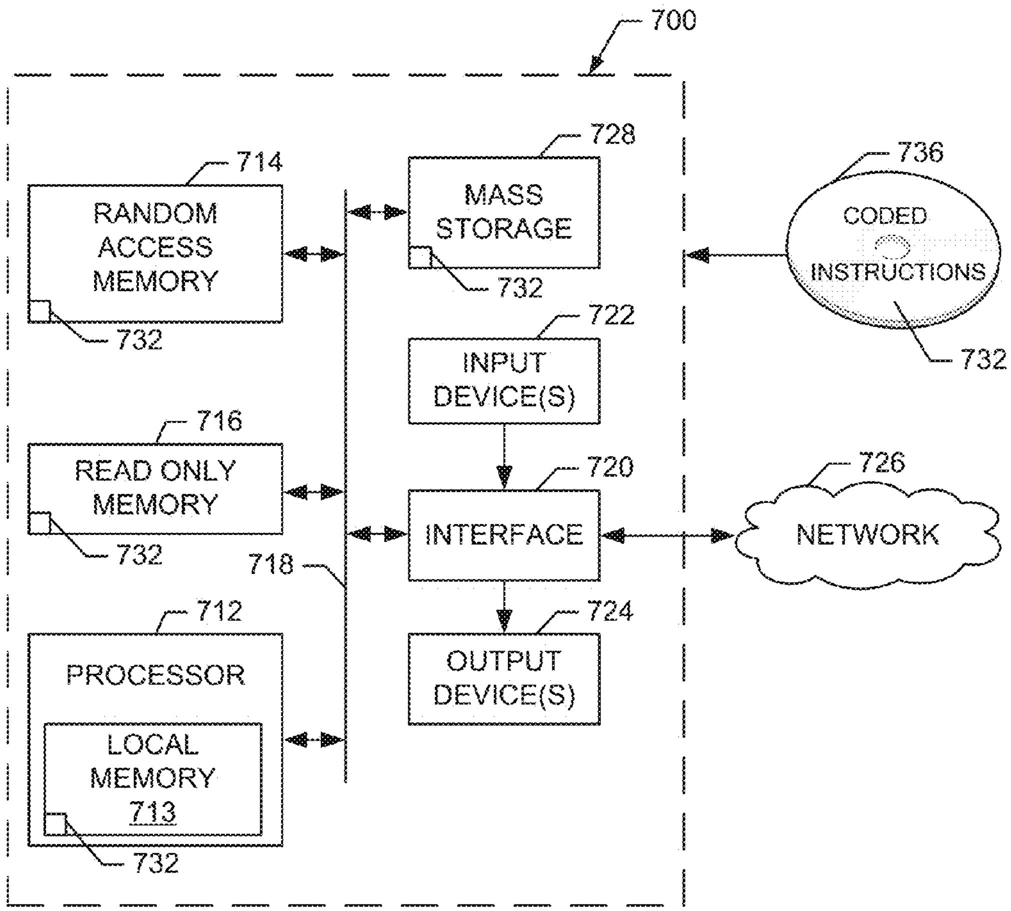
FIG. 7 is a block diagram of an example processor platform that may execute the example machine readable instructions of FIGS. 4, 5 and/or 6 to implement the example system of FIG. 1, the example audio source of FIGS. 1 and/or 2, and/or the example user device of FIGS. 1 and/or 3.

FIG. 7 is a block diagram of an example processor platform 700 capable of executing instructions of FIGS. 4-6 to implement the example audio suppression system 100, the example audio source 105, the example user device(s) 110, the example configuration interface 135, the example audio input interfaces 205, the example audio amplifier 210, the example wireless transmitter 215, the example audio processor 220, the example audio formatter 225, the example audio delayer 230, the example audio sensor interface 305, the example audio output driver 310, the example wireless receiver 315, the example audio suppression processor 320, the example audio delay compensator 330, the example audio equalizer 335, the suppression signal generator 340, the example suppression activation interface 345 and/or the example configuration interface 350 of FIGS. 1-3. The processor platform 700 can be, for example, a server, a personal computer, a mobile device (e.g., a cell phone, a smart phone, a tablet such as an iPad), a personal digital assistant (PDA), an Internet appliance, a DVD player, a CD player, a digital video recorder, a Blu-ray player, a gaming console, a personal video recorder, a set top box a digital camera, or any other type of computing device.

The processor platform 700 of the illustrated example includes a processor 712. The processor 712 of the illustrated example is hardware. For example, the processor 712 can be implemented by one or more integrated circuits, logic circuits, microprocessors or controllers from any desired family or manufacturer.

The processor 712 of the illustrated example includes a local memory 713 (e.g., a cache) (e.g., a cache). The processor 712 of the illustrated example is in communication with a main memory including a volatile memory 714 and a non-volatile memory 716 via a link 718. The link 718 may be implemented by a bus, one or more point-to-point connections, etc., or a combination thereof. The volatile memory 714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 716 may be implemented by flash memory and/or any other desired type of memory device. Access to the main memory 714, 716 is controlled by a memory controller.

The processor platform 700 of the illustrated example also includes an interface circuit 720. The interface circuit 720 may be implemented by any type of interface standard, such as an Ethernet interface, a universal serial bus (USB), and/or a PCI express interface.

In the illustrated example, one or more input devices 722 are connected to the interface circuit 720. The input device(s) 722 permit(s) a user to enter data and commands into the processor 712. The input device(s) can be implemented by, for example, an audio sensor, a microphone, a camera (still or video), a keyboard, a button, a mouse, a touchscreen, a track-pad, a trackball, a trackbar (such as an isopoint), a voice recognition system and/or any other human-machine interface.

One or more output devices 724 are also connected to the interface circuit 720 of the illustrated example. The output devices 724 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 720 of the illustrated example, thus, typically includes a graphics driver card, a graphics driver chip or a graphics driver processor.

The interface circuit 720 of the illustrated example also includes a communication device such as a transmitter, a receiver, a transceiver, a modem and/or network interface card to facilitate exchange of data with external machines (e.g., computing devices of any kind) via a network 726 (e.g., an Ethernet connection, a digital subscriber line (DSL), a telephone line, coaxial cable, a cellular telephone system, etc.).

The processor platform 700 of the illustrated example also includes one or more mass storage devices 728 for storing software and/or data. Examples of such mass storage devices 728 include floppy disk drives, hard drive disks, compact disk drives, Blu-ray disk drives, RAID (redundant array of independent disks) systems, and digital versatile disk (DVD) drives.

Coded instructions 732 corresponding to the instructions of FIGS. 4-6 may be stored in the mass storage device 728, in the volatile memory 714, in the non-volatile memory 716, in the local memory 713 and/or on a removable tangible computer readable storage medium, such as a CD or DVD 736.

At least some of the above described example methods and/or apparatus are implemented by one or more software and/or firmware programs running on a computer processor. However, dedicated hardware implementations including, but not limited to, application specific integrated circuits, programmable logic arrays and other hardware devices can likewise be constructed to implement some or all of the example methods and/or apparatus described herein, either in whole or in part. Furthermore, alternative software implementations including, but not limited to, distributed processing or component/object distributed processing, parallel processing, or virtual machine processing can also be constructed to implement the example methods and/or apparatus described herein.

To the extent the above specification describes example components and functions with reference to particular standards and protocols, it is understood that the scope of this patent is not limited to such standards and protocols. For instance, each of the standards for Internet and other packet switched network transmission (e.g., Transmission Control Protocol (TCP)/Internet Protocol (IP), User Datagram Protocol (UDP)/IP, HyperText Markup Language (HTML), HyperText Transfer Protocol (HTTP)) represent examples of the current state of the art. Such standards are periodically superseded by faster or more efficient equivalents having the same general functionality. Accordingly, replacement standards and protocols having the same functions are equivalents which are contemplated by this patent and are intended to be included within the scope of the accompanying claims.

Additionally, although this patent discloses example systems including software or firmware executed on hardware, it should be noted that such systems are merely illustrative and should not be considered as limiting. For example, it is contemplated that any or all of these hardware and software components could be embodied exclusively in hardware, exclusively in software, exclusively in firmware or in some combination of hardware, firmware and/or software. Accordingly, while the above specification described example systems, methods and articles of manufacture, the examples are not the only way to implement such systems, methods and articles of manufacture. Therefore, although certain example methods, apparatus and articles of manufacture have been described herein, the scope of coverage of this patent is not limited thereto. On the contrary, this patent covers all methods, apparatus and articles of manufacture fairly falling within the scope of the claims either literally or under the doctrine of equivalents.

What is claimed is:

1. A method for audio suppression, the method comprising:

obtaining, at a first time, reference audio data corresponding to a first audio signal, the first audio signal to be output by an audio source at a second time later than the first time;

processing, with a processor, the reference audio data to generate a suppression signal to be output by a speaker associated with a user device to suppress the first audio signal when the first audio signal is received at the user device at a third time later than the first time, the processing including:

estimating a second time delay determined to compensate for an audio propagation delay between the audio source and the user device, the audio propagation delay corresponding to a difference between the second time and the third time;

delaying the reference audio data by a first time delay and the second time delay; and inverting the reference audio data; and providing the suppression signal to an audio output driver in communication with the speaker.

2. The method of claim 1, wherein the obtaining of the reference audio data includes receiving the reference audio data wirelessly from the audio source, and the first time delay is a constant value set to compensate for an expected time interval between the first time and the second time.

3. The method of claim 2, wherein the processing of the reference audio data further includes:

estimating an audio level of the first audio signal at the user device; and scaling the reference audio data based on the audio level.

4. The method of claim 3, further including obtaining sensed audio data from a microphone of the user device, wherein the estimating of the second time delay includes processing the sensed audio data to estimate the audio propagation delay, and the estimating of the audio level includes processing the sensed audio data to estimate the audio level.

5. The method of claim 2, further including obtaining configuration data specifying the first time delay, the configuration data being received wirelessly from the audio source.

6. The method of claim 1, further including receiving an activation signal to selectively enable the processing of the reference audio data to generate the suppression signal.

7. The method of claim 1, wherein the audio signal is a first audio signal, and further including combining the suppression signal with a second audio signal to be output by the speaker.

8. The method of claim 1, wherein the user device is a headset to be worn by a user.

9. A tangible machine readable storage medium including machine readable instructions which, when executed, cause a processor of a user device to perform operations comprising:

obtaining, at a first time, reference audio data corresponding to a first audio signal, the first audio signal to be output by an audio source at a second time later than the first time;

processing the reference audio data to generate a suppression signal to be output by a speaker associated with the user device to suppress the first audio signal when the first audio signal is received at the user device at a third time later than the first time, the processing including:

estimating a second time delay determined to compensate for an audio propagation delay between the audio source and the user device, the audio propagation delay corresponding to a difference between the second time and the third time;

delaying the reference audio data by a first time delay and the second time delay; and inverting the reference audio data; and providing the suppression signal to an audio output driver in communication with the speaker.

10. The storage medium of claim 9, wherein the obtaining of the reference audio data includes receiving the reference audio data wirelessly from the audio source, and the first time delay is a constant value set to compensate for an expected time interval between the first time and the second time.

11. The storage medium of claim 10, wherein the processing of the reference audio data further includes:

estimating an audio level of the first audio signal at the user device; and scaling the reference audio data based on the audio level.

12. The storage medium of claim 11, wherein the operations further include obtaining sensed audio data from a microphone of the user device, the estimating of the second time delay includes processing the sensed audio data to estimate the audio propagation delay, and the estimating of the audio level includes processing the sensed audio data to estimate the audio level.

13. The storage medium of claim 9, wherein the operations further include receiving an activation signal to selectively enable the processing of the reference audio data to generate the suppression signal.

14. The storage medium of claim 9, wherein the audio signal is a first audio signal, and the operations further include combining the suppression signal with a second audio signal to be output by the speaker.

15. A user device comprising:

a headset including a speaker and an audio output driver in communication with the speaker;

a memory including machine readable instructions;

a processor to execute the instructions to perform operations including:

obtaining, at a first time, reference audio data corresponding to a first audio signal, the first audio signal to be output by an audio source at a second time later than the first time;

processing the reference audio data to generate a suppression signal to be output by the speaker of the headset to suppress the first audio signal when the first audio signal is received at a third time later than the first time, the processing including:

estimating a second time delay determined to compensate for an audio propagation delay between the audio source and the user device, the audio propagation delay corresponding to a difference between the second time and the third time;

delaying the reference audio data by a first time delay and the second time delay; and inverting the reference audio data; and providing the suppression signal to the audio output driver.

16. The user device of claim 15, wherein the obtaining of the reference audio data includes receiving the reference audio data wirelessly from the audio source, and the first time delay is a constant value set to compensate for an expected time interval between the first time and the second time.

17. The user device of claim 16, wherein the processing of the reference audio data further includes:

estimating an audio level of the first audio signal at the user device; and scaling the reference audio data based on the audio level.

18. The user device of claim 17, further including a microphone, wherein the operations further include obtaining sensed audio data from the microphone, the estimating of the second time delay includes processing the sensed audio data to estimate the audio propagation delay, and the estimating of the audio level includes processing the sensed audio data to estimate the audio level.

19. The user device of claim 15, wherein the operations further include receiving an activation signal to selectively enable the processing of the reference audio data to generate the suppression signal.

20. The user device of claim 15, wherein the audio signal is a first audio signal, and the operations further include combining the suppression signal with a second audio signal to be output by the speaker.

* * * * *